United States Patent
Cerra et al.

(10) Patent No.: US 8,703,071 B2
(45) Date of Patent: Apr. 22, 2014

(54) SYRINGE SYSTEM

(75) Inventors: Reno Cerra, Ringwood (AU); Mark David Wardle, Ringwood (AU); Brenden Anthony Shawcroft, Ringwood (AU); James Marcus Lachlan Thompson, Ringwood (AU)

(73) Assignee: ETP Mass Spectrometry Pty Ltd, Ringwood, Victoria (AU)

( * ) Notice: Subject to any disclaimer, the term of this patent is extended or adjusted under 35 U.S.C. 154(b) by 792 days.

(21) Appl. No.: 12/682,565

(22) PCT Filed: Sep. 8, 2008

(86) PCT No.: PCT/AU2008/001331
§ 371 (c)(1),
(2), (4) Date: Apr. 9, 2010

(87) PCT Pub. No.: WO2009/046482
PCT Pub. Date: Apr. 16, 2009

(65) Prior Publication Data
US 2010/0247378 A1   Sep. 30, 2010

(30) Foreign Application Priority Data

Oct. 10, 2007   (AU) ................ 2007905543

(51) Int. Cl.
*B01L 3/02* (2006.01)
*G01N 1/14* (2006.01)
*G01N 35/10* (2006.01)

(52) U.S. Cl.
USPC ...... 422/509; 422/501; 73/864.14; 73/864.25

(58) Field of Classification Search
USPC ............ 422/501, 509, 521–522, 511; 73/864.13–864.14, 864.16–864.17, 73/864.24–864.25
See application file for complete search history.

(56) References Cited

U.S. PATENT DOCUMENTS

| | | | |
|---|---|---|---|
| 3,693,484 A | | 9/1972 | Sanderson, Jr. |
| 4,487,081 A | * | 12/1984 | De Vaughn et al. ........ 73/864.13 |
| 4,561,682 A | | 12/1985 | Tisserat |
| 4,663,796 A | | 5/1987 | Helling et al. |
| 4,906,123 A | | 3/1990 | Weskamp et al. |
| 5,211,501 A | | 5/1993 | Nakamura et al. |
| 5,230,538 A | | 7/1993 | Kobayashi |
| 5,308,331 A | | 5/1994 | Avila et al. |
| 5,462,316 A | | 10/1995 | Street et al. |
| 5,531,693 A | | 7/1996 | Vounatsos |

(Continued)

FOREIGN PATENT DOCUMENTS

| | | |
|---|---|---|
| WO | 2005124366 A1 | 12/2005 |
| WO | WO 2006/083695 A2 * | 8/2006 |

*Primary Examiner* — Jan Ludlow
(74) *Attorney, Agent, or Firm* — Fulwider Patton LLP

(57) ABSTRACT

Syringe mounting apparatus includes a body (25,300), and a coupling mechanism (20) on the body having a housing (22) to receive a barrel of a syringe component and means (28) to detachably engage the barrel and thereby interchangeably retain the syringe component. A plunger connector (60) is positioned with respect to the housing for operably coupling a plunger driver to a plunger element in the barrel of a syringe component when it is interchangeably retained by the coupling mechanism. The plunger connector includes means (74) for detachably engaging the plunger element in a manner allowing the plunger driver to effect reciprocatory movement of the plunger element longitudinally of the barrel for drawing fluid into or expelling fluid from the syringe component. Also disclosed are a syringe system, a disposable syringe component, and a syringe component with engagement features.

25 Claims, 11 Drawing Sheets

(56) References Cited

U.S. PATENT DOCUMENTS

| | | |
|---|---|---|
| 5,833,660 A | 11/1998 | Nathan et al. |
| 6,379,072 B1 | 4/2002 | Brown et al. |
| 6,973,846 B2 | 12/2005 | Bremer et al. |
| 7,056,301 B2 | 6/2006 | Liu |
| 2002/0173750 A1 | 11/2002 | Huang et al. |
| 2004/0022680 A1 | 2/2004 | Gueller et al. |

* cited by examiner

SYRINGE SYSTEM

CROSS-REFERENCES TO RELATED APPLICATIONS

This is a U.S. national phase of PCT/AU/2008/001331, filed 8 Sep. 2008, claiming priority from Australian Application No. AU 2007905543, filed 10 Oct. 2007.

FIELD OF THE INVENTION

The present invention relates generally to syringe mounting apparatus optionally having application to analytical syringe systems such as auto-sampler systems. In one aspect, the invention is concerned with reducing and preferably eliminating the risk of cross contamination or sample carry-over associated with sampling using an analytical syringe.

BACKGROUND OF THE INVENTION

In the field of analytical science, auto-samplers have made a significant impact on the efficiency, speed and reproducibility of sample processing and injection into analytical instrumentation. Despite these benefits there remains a significant challenge on improving the reduction of sample carryover or cross contamination to a level of eliminating it altogether. The elimination of carry over in auto-samplers is essential for the analysis of clinical samples as well as samples that carry a broad dynamic range of analytes, such as blood plasma, where the range in concentration of analytes can be as large as $10^{10}$ to $10^{12}$ between the least and most abundant proteins.

The problems associated with the risk of sample carry over can be so significant that only a truly disposable injection system will suffice. Where sample injection volumes are small, for e.g. <2 μl, it is possible to limit the aspiration of a sample to the surfaces of the auto-sampler syringe needle and dispose of the needle between samples. To a great extent, disposable polypropylene tips meet this need, but they are not of sufficient rigidity to pierce the sample vial septa nor are they of the correct design to interface with the typical analytical instrument's injection port. Hence, a metal needle is considered necessary.

For samples greater than the internal volume of the needle or disposable tip, the sample inevitably contacts the internal surfaces of the precision analytical syringe barrel and plunger tip. Once this occurs it is essential to wash the syringe rigorously to remove any risk of sample cross contamination. In the field of clinical assays the perceived risk is so high that disposal of each syringe is sometimes preferable, albeit at great expense with presently available analysis systems.

Another issue with current auto-samplers is their relative lack of flexibility. They typically have fixed arrays of syringes arranged in gantry style on a robotic arm or as discrete moveable heads. In general, these auto-samplers are designed to carry out preprogrammed repetitive bulk analysis tasks at standard uniform sample volumes, and are not easily adaptable to rapid interchangeability between tasks. This issue is addressed in one way by the system disclosed in international patent publication WO 2005/124366, in which a multi-axis transport mechanism selectively moves syringe devices among multiple analysis stations at each of which the devices are detached. Each syringe device is a self-contained "smart" sample probe with an inbuilt motor and controller to effect aspiration and/or dispensing operations. This approach is sophisticated in concept and execution but unduly so far many requirements.

The present inventors have realised that it is possible to develop an improved syringe mounting apparatus and analysis system that are capable of addressing both of the above-mentioned deficiencies with present auto-sampler configurations.

SUMMARY OF THE INVENTION

In a first aspect, the invention provides syringe mounting apparatus that includes a body and a coupling mechanism on the body having a housing to receive a barrel of a syringe component and means to detachably engage the barrel and thereby interchangeably retain the syringe component. A plunger connector is positioned with respect to the housing for operably coupling a plunger driver to a plunger element in the barrel of a syringe component when it is interchangeably retained by the coupling mechanism. The plunger connector includes means for detachably engaging the plunger element in a manner allowing the plunger driver to effect reciprocatory movement of the plunger element longitudinally of the barrel for drawing fluid into or expelling fluid from the syringe component.

The coupling mechanism may include a sleeve and first resiliently retractable elements or formations, for example spring-loaded balls, retained by the sleeve engageable with co-operating formations on a barrel of a syringe component. Preferably, means is provided to lock the elements or formations against retraction, whereby to lock a barrel engaged thereby in the coupling mechanism.

For use with syringe components having a plunger element in the form of a plunger tip, the plunger connector may further include an elongate plunger arranged to reciprocate longitudinally through the coupling mechanism and within the barrel of the syringe component. This plunger has a head portion that includes within the barrel the means for detachably engaging the plunger tip.

For use with a syringe component having a plunger element that projects from the barrel, the plunger connector may comprise a housing to receive the plunger element and means to detachably engage the plunger element. In this case, the means to detachably engage the plunger element may comprise a sleeve assembly and second resiliently retractable elements or formations, for example spring-loaded balls, within the sleeve assembly engageable with co-operating formations on the plunger element.

The coupling mechanism may include an adaptor having a first portion interchangeably receivable by and detachably engageable with the coupling mechanism, and a second portion detachably engageable with a barrel of a syringe component too small to be interchangeably retained by the coupling mechanism. The adaptor has a longitudinally extending cavity therethrough for the plunger element and/or plunger connector. For use with syringe components having a plunger element in the form of a plunger tip, the plunger connector may further include an elongate plunger mounted in the adaptor cavity and arranged to reciprocate longitudinally through the coupling mechanism and within the barrel of the syringe component, the plunger tip having a tip portion that includes within the barrel the means for detachably engaging the plunger tip.

For wider applications, especially retrofit applications, the first portion of the adaptor may be interchangeable for other syringe mounting formations.

The invention in its first aspect further extends to an analytical syringe system comprising structure that includes said plunger driver and that supports syringe mounting apparatus as aforedescribed for movement laterally and vertically in a work space, and control means programmable or programmed for selectively effecting said movement, for operating the plunger driver, and to selectively engage and disengage successive syringe components.

The analytical syringe system may include a plurality of re-usable syringe components detachably engageable by and thereby interchangeably retainable by the coupling mechanism, and/or a plurality of disposable syringe components detachably engageable by and thereby interchangeably retainable by said coupling mechanism. The disposable syringe components may each be in accordance with the second aspect of the invention described below.

The invention further provides syringe apparatus that includes one or more disposable syringe components that each include a syringe barrel, a hollow needle projecting from an end of the barrel, and a syringe plunger tip sealingly slidable in the barrel for drawing fluid into the needle or expelling fluid through the needle. A syringe pick-up head includes at least a plunger mounted for longitudinal reciprocatory movement for driving the plunger tip to slide in the barrel. Means is provided for detachably engaging a disposable syringe element to the syringe pick-up head with the plunger in co-operatively driving engagement with the plunger tip.

In its first aspect, the invention further provides syringe apparatus comprising:
a housing;
a projecting plunger mounted for longitudinal reciprocatory movement; and
means on the housing to receive and detachably engage with a disposable syringe component that includes a syringe barrel, a hollow needle projecting from an end of the barrel and a syringe plunger tip sealingly slidable in the barrel for drawing fluid into the needle or expelling fluid through the needle; wherein said plunger and said detachable engagement are such that the plunger is in co-operating driving engagement with the plunger tip.

The detachable engagement between the plunger tip and the plunger is preferably by means of a socket portion on one, more preferably the plunger tip, and a complementary spigot portion on the other. Engagement and disengagement preferably entails deformation of one or other, or both, of the socket portion or the spigot portion, and advantageously entails a snap action.

The barrel of the disposable syringe component preferably includes a stop positioned to be struck by the plunger tip as it is relatively withdrawn in its barrel by the travelling plunger, whereby to effect disengagement of the plunger tip from the plunger.

Means is preferably provided for detachably coupling the syringe pick-up head and the barrel of the disposable syringe component. Such means may comprise a sleeve and co-operating formations, for example plural spring-loaded balls and complementary recesses or vice versa, on the sleeve and barrel.

The disposable syringe component preferably has a strike face engageable by a step or the like to effect disengagement of the disposable syringe component from the syringe pick-up head on withdrawal of the latter relative to the stop. The syringe apparatus advantageously includes a stop for this purpose.

In a preferred embodiment, the syringe pick-up head is a travelling head of a robotic auto-sampler programmable or programmed to effect movements of the head to selectively engage and disengage successive disposable syringe components.

In a second aspect, the invention provides a disposable syringe component comprising a syringe barrel, a hollow needle projecting from an end of the barrel, a syringe plunger tip sealingly slidable in the barrel for drawing fluid into the needle or expelling fluid through the needle, and means on the plunger tip detachably engageable with a plunger for driving the plunger tip to slide in the barrel.

The plunger tip may have a socket portion deformable to receive an end formation of a plunger.

The barrel of the disposable syringe component may include a stop positioned to be struck by the plunger tip as it is relatively withdrawn in its barrel by the travelling plunger, whereby to effect disengagement of the plunger tip from the plunger.

Preferably the disposable syringe component has a strike face engageable by a step or the like to effect disengagement of the disposable syringe component from syringe mounting apparatus by which it is held, on withdrawal of the syringe mounting apparatus relative to the stop.

Preferably, the barrel of the disposable syringe component is selected from the group consisting of borosilicate glass, polypropylene, Delrin or the like. Preferably, the syringe plunger tip of the disposable syringe component is selected from the group consisting of PTFE (Teflon), UHMWPE (Ultra High Molecular Weight Poly Ethylene), and Ekonol filled PTFE.

In a still further aspect, the invention provides a syringe component comprising a syringe barrel, a hollow needle projecting from an end of the barrel, and a syringe plunger sealingly slidable in the barrel for drawing fluid into the needle or expelling fluid through the needle. A formation on the syringe barrel is detachably engageable with a coupling mechanism for transport of the syringe component, and a formation on the plunger is detachably engageable with a plunger for driving the plunger to slide in the barrel while the syringe barrel is engaged with the coupling mechanism.

Throughout the specification, unless the context requires otherwise, the word "comprise", or variations such as comprises or comprising, will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

In order that the present invention may be more clearly understood, preferred forms will be described with reference to the following examples and accompanying drawings.

DETAILED DESCRIPTION OF THE EMBODIMENTS

Figure 1:
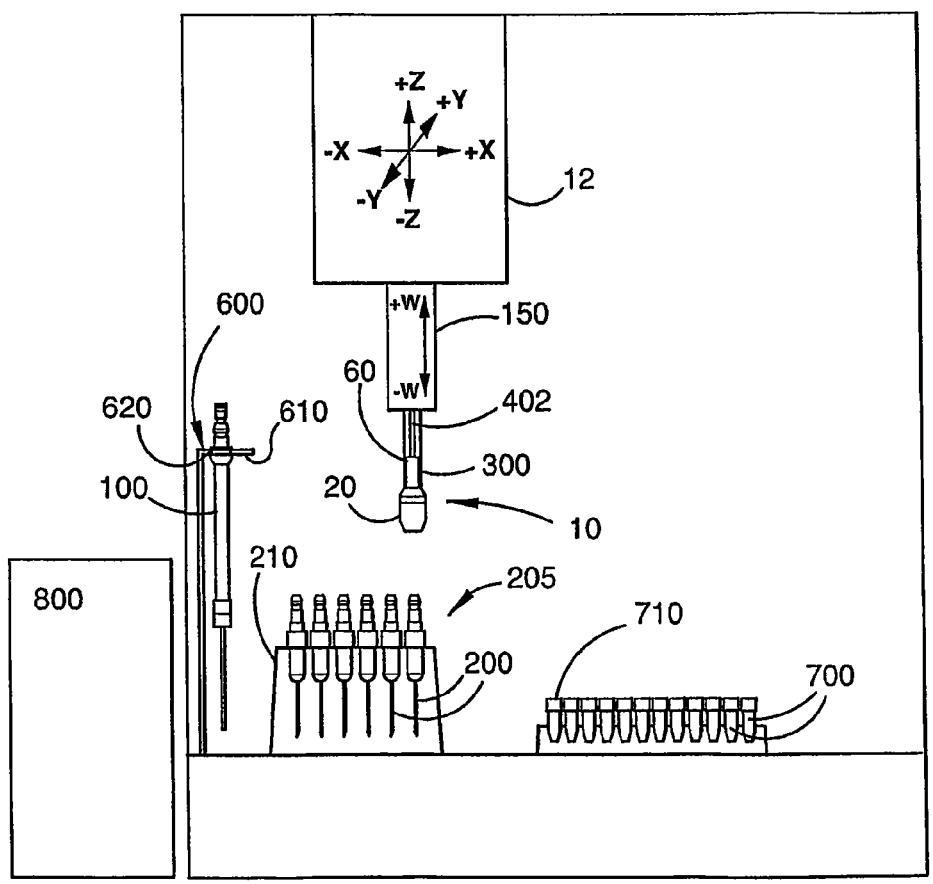
FIG. 1 is a schematic not-to-scale representation in elevation of the layout of an analytical syringe system, incorporating syringe mounting apparatus according to the present invention.

The analytical syringe system depicted in FIG. 1 includes a multi-axis auto-sampler 12, and an array 205 of syringe components including washable and reusable syringe components 100 retained upright in a stand 600 and disposable components 200 retained in stand 210. Syringe mounting apparatus 10 is provided on a translatable syringe pick-up head 300 depending from auto-sampler 12 and has a syringe coupling mechanism 20 and a plunger connector 60. The latter is carried by a w-axis plunger driver 402 at its lower end for vertical, i.e. longitudinal, reciprocal movement relative to coupling mechanism 20. Stand 600 also defines a fixed position 610 at which a disposable syringe component may be detached from pick-up head 300 for disposal. It will be appreciated that FIG. 1 is not to scale.

Figure 11:
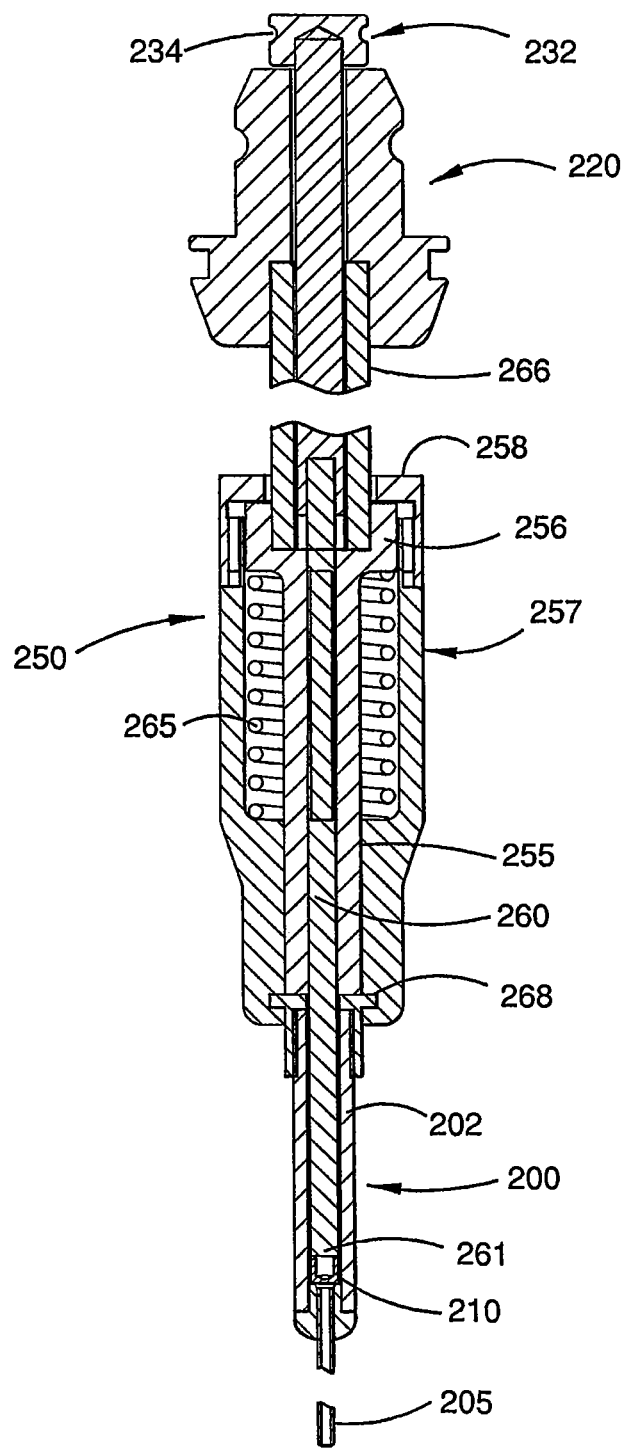
FIG. 11 is an axial cross-section of an assembly of a small-volume disposable syringe component according to an embodiment of the second aspect of the invention and an adaptor by which the syringe mounting apparatus of FIGS. 2 and 3 may interchangeably engage the disposable syringe component.

In a first embodiment of the invention; the syringe mounting apparatus 10 comprising coupling mechanism 20 and plunger connector 60 is configured to detachably and interchangeably directly engage and pick up one of multiple larger volume re-usable syringe components 100 (FIG. 4), or, by means of an adaptor 250, successive disposable smaller-volume syringe components 200 (FIG. 11).

Figure 3:
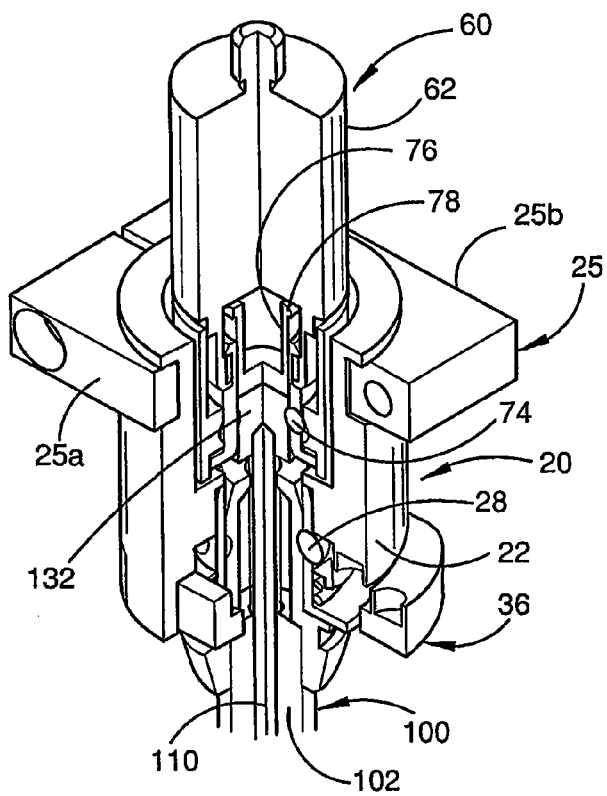
FIG. 3 is a cut-away partial isometric view of the apparatus depicted in FIG. 2.
Figure 5:
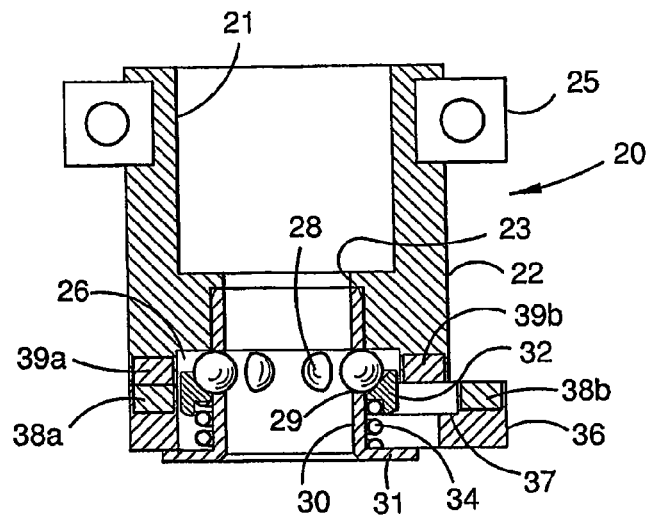

As best seen in FIGS. 3 and 5, coupling mechanism 20 includes a generally cylindrical hollow housing 22 with an upper peripheral external groove 24 that received the two halves 25a, 25a of a clamp device 25 by which the housing is suspended from pick-up head 300.

At the other, lower, end of housing 22, a counterbore 26 houses a ring of spaced balls 28 retained in holes 29 of a co-axial sleeve 30. Sleeve 30 is firmly secured by an interference fit in an annular rebate from the main bore 23 of housing 22. Holes 29 are sized and shaped so that the balls 28 protrude inwardly from them but cannot pass through, and the balls are biased to this position by a ring 32. Ring 32 is axially slidable about the outside of sleeve 30, seats balls 28 obliquely and is biased against the balls by a helical compression spring 34 retained between ring 32 and a peripheral flange 31 of sleeve 30 that abuts the rim of housing 22.

Balls 28 are lockable into the illustrated protruding position by a slide member 36 that is transversely moveable between an inactive position (FIG. 5) and an active position (FIG. 7) in which a shoulder 37 on the slide underlies the lower rim of ring 32 at one side and prevents it from sliding downwardly against spring 34. The two positions of slide 36 are indexed by respective pairs of magnets 38a,39a; 38b,39b in the upper surface of the slide and in an opposing downwardly facing surface of housing 22.

Figure 6:
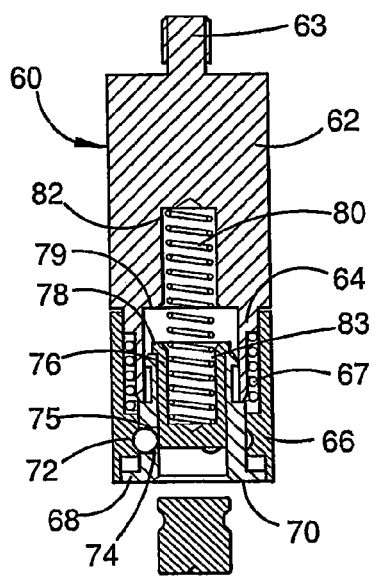

Plunger connector 60 (FIGS. 2, 3 and 6) includes a solid cylindrical main body 62 with a central upstanding post 63 by which the main body 62 is linked to w-axis plunger driver 402 of the auto-analyser pick-up head 300. At its other, lower, end, body 62 has an integral depending thin-walled annular partition 64 that is offset inwardly to define an outer seat for an outer, axially slidable, collar 66 and an inner seat for a helical compression spring 67.

An inner, fixed, collar 68 threadably engages an inner threaded portion of partition 64 and has a peripheral inner end flange 70 that defines a lower limit of travel for collar 66. Collar 66 is biased to this limit by spring 67 and has an inside annular groove 72 that receives respective balls 74 retained in holes 75 in collar 68 from which the balls 74 can protrude but not pass through.

The assembly is completed by an inner plunger abutment member 76 slidably moveable within collar 68 between a lower limit at which a peripheral lip 78 at the upper rim of the abutment member abuts the upper rim of collar 68, and an upper limit adjacent an inner endface 79 of body 62. Abutment member 76 is biased to the lower limit by a helical compression spring 80 retained in blind bores 82, 83 in body 62 and abutment member 76.

Figure 4:
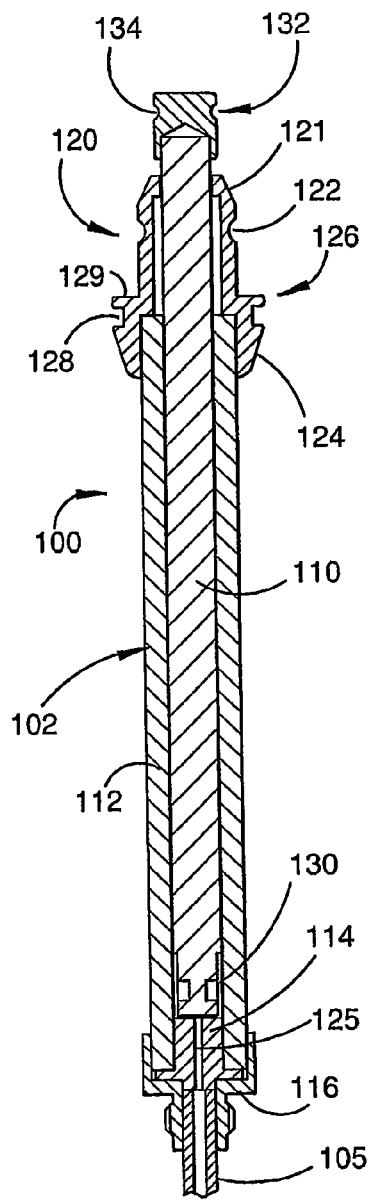
FIGS. 4, 5 and 6 are respective axial cross-sectional views of the syringe component, the coupling mechanism and the plunger connector as seen in FIGS. 2 and 3.

A typical interchangeable syringe component 100 is shown in FIG. 4. It has an elongate barrel 102, a projecting hollow needle 105, and a plunger 110 longitudinally slidable within the barrel for aspirating liquid sample into needle 105, and usually also barrel 102, and/or injecting liquid sample from the needle. Barrel 102 includes a precision made tubular glass body 112, an end insert seal 114 at one end of body 112 with a fine aperture 125 therethrough, an endpiece 116 in which the needle is mounted, and, at the other end of body 112, an end fitting 120 dimensioned for engagement with coupling mechanism 20.

End fitting 120 has a tubular forward portion with an external end taper 121 and a peripheral groove 122 of arcuate cross-section to receive balls 28 of the coupling mechanism. A rearward skirt 124 is fitted about the end of glass body 112 and an intermediate portion 126 defines a second groove 128 of rectangular cross-section and an annular shoulder 129.

The inner end of plunger 110 has an end cap 130 that sealingly slidably engages the inner surface of glass body 112 in the usual manner. The plunger's outer end has an end piece 132 dimensioned for receipt within inner collar 68 of plunger connector 60, and provided with a peripheral groove 134 of arcuate cross-section to receive balls 74 of the plunger connector.

When it is desired to pick up a re-usable syringe 100 for performing an aspiration/injection operation, pick up head 300 is moved into position over a selected syringe in array 600. The sequence of operations is depicted in FIGS. 8a, 8b and 2 or 3. The plunger driver 402 positions plunger connector 60 at a position just projecting into an enlarged concentric cavity 21 in the upper part of housing 22 (refer FIG. 5).

Housing 22 moves down onto and about the syringe component 100 (FIG. 8a) until end taper 21 pushes balls 28 back through holes 29, from which they are subsequently pushed by spring 34 into grooves 122 (FIG. 8b): at this point flange 31 strikes shoulder 129 to limit downward movement of the coupling housing 22. Driver 402 now brings the driver connector onto plunger end piece 132, which relatively pushes back plunger abutment member 76 (against spring 80) to expose balls 74 for engagement in groove 134: this motion allows spring 67 to push collar 66 down to prevent release of balls 74 and so lock the parts together.

Figure 7:
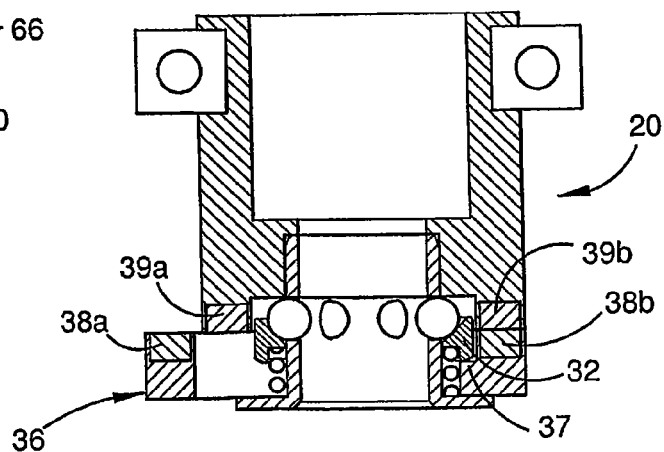
FIG. 7 is a view similar to FIG. 5 but showing the locking slide in its locking condition.
Figure 8A:
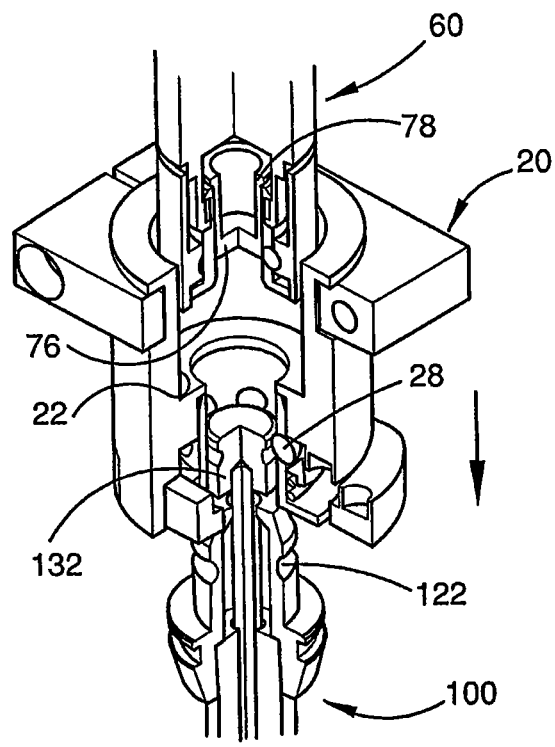
FIGS. 8a and 8b are views similar to FIG. 3 showing successive stages in the process of engaging the syringe mounting apparatus with an interchangeable syringe component.
Figure 8B:
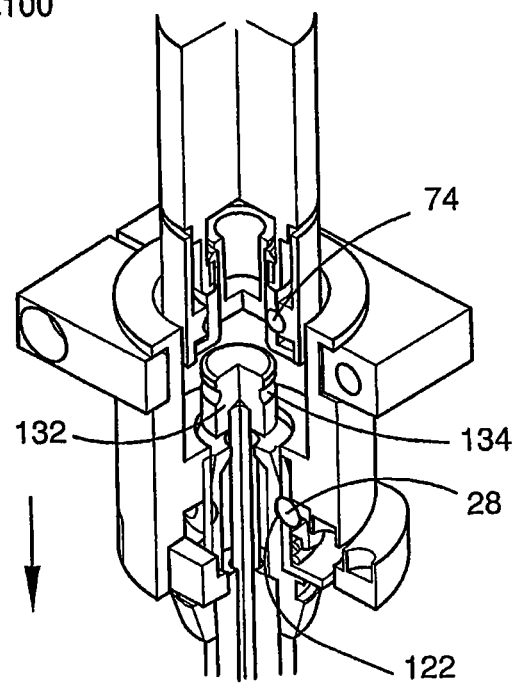
Figure 9:
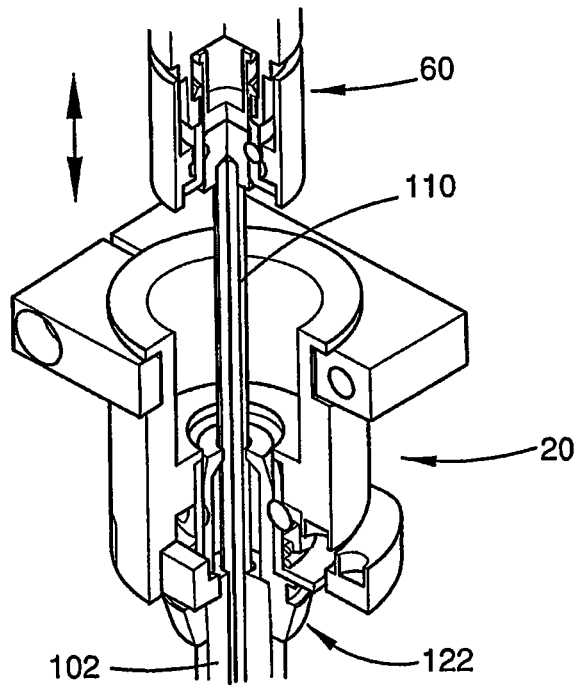
FIG. 9 is a view similar to FIG. 3 but with the plunger connector, and the plunger element of the interchangeable syringe component displaced upwardly.

As the syringe component 100 is now drawn out of stand 600 by pick-up head 300, a magnet on the stand draws slide member 36 to the locking position depicted in FIG. 7. The picked up syringe component 100 can now be translated to one or more selected vials and one or more instrument ports, e.g. an injection port of an analyser, moved vertically in the z-axis (e.g. to drive needle 105 to pierce a vial) and driver 402 operated to aspirate sample into the syringe component 100 (FIG. 9) or to inject sample therefrom (e.g. into an injection port of an analyser). Performed operations may of course include washing the re-usable syringe component at a washing station. The analyser may be one or more of a gas chromatograph, a liquid chromatograph, a mass spectrometer or any combination of two or more of these.

Figure 10:
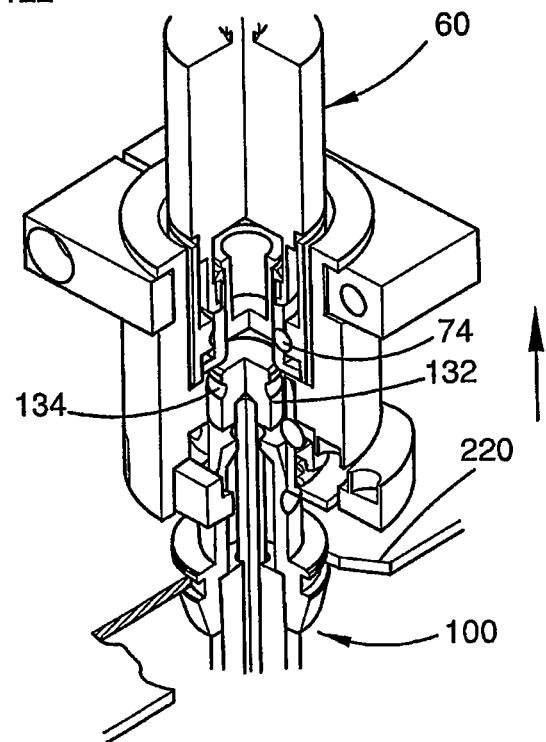
FIG. 10 is a view similar to FIG. 3 during disengagement of the syringe apparatus from the interchangeable syringe component.

When operations are complete and it is desired to exchange the syringe component for another (e.g. a freshly washed syringe component or a syringe component of different volume) disengagement is effected by returning the syringe component to a cutout 610 on a projecting plate 620 of stand 600, or another stand, at which the rim 220 of a recess engages groove 128 of the syringe barrel end fitting 120 (FIG. 10). During this movement, slide member 36 is engaged and pushed to its inactive position (FIG. 5). A small downward push by driver 402 will relatively push back collar 66 and allow balls 74 to be pushed outwardly into groove 72 as the pick-up head is raised. This disengages the plunger from the plunger connector, while the retraction of balls 28 from groove 122 simultaneously disengages the barrel end-fitting 120 from coupling mechanism 20 (FIG. 10).

Instead of picking up washable/re-usable syringe components 100, pick-up head 300 may be employed to engage smaller volume disposable syringe elements 200.

Because these disposable syringe components 200 are typically of smaller volume and therefore smaller overall dimensions than syringe components 100, an adaptor 250 is necessary, firstly to allow engagement with coupling mechanism 20, and secondly to provide a further plunger connector element to couple the plunger driver to a plunger element in the barrel of the syringe component (FIG. 11).

Figure 12:
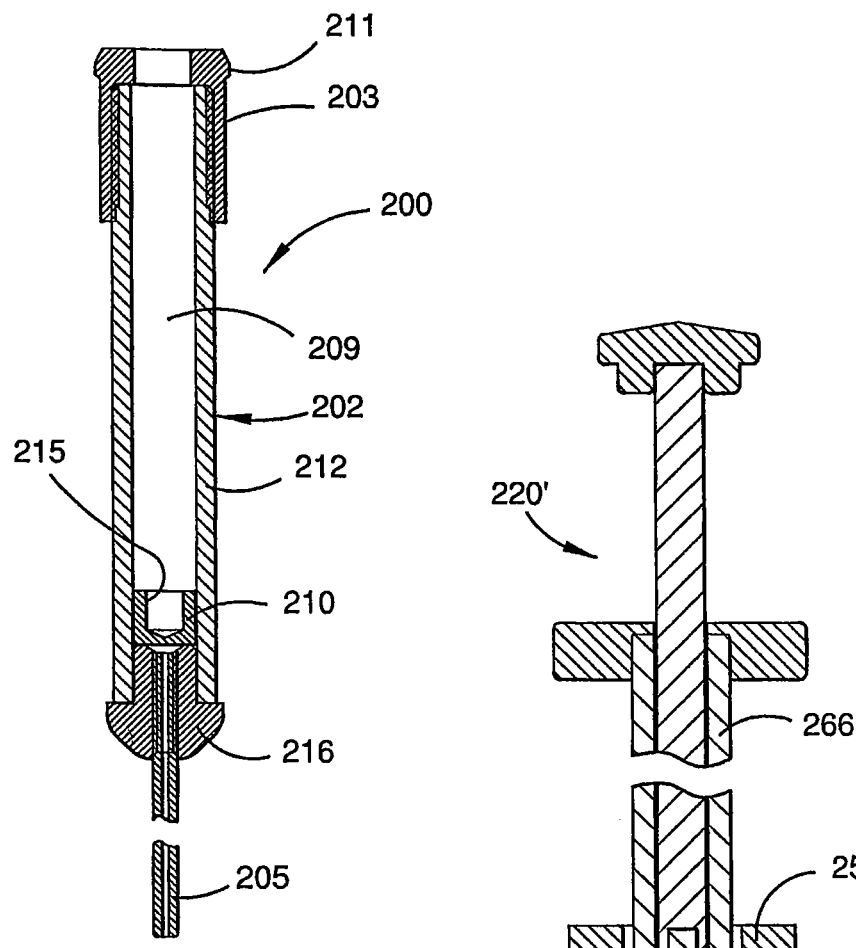
FIG. 12 is an axial cross-section of the disposable syringe component depicted in FIG. 11.

A typical disposable syringe element 200 is illustrated in FIG. 12. It comprises a barrel 202 about an interior cavity 209, a hollow needle 205 that projects from a closed end of barrel 202 so that fluid may be drawn into cavity 209 or expelled from the cavity through the needle, and a plunger tip 210. Tip 210 is sealingly slidable in cavity 209 for drawing fluid into needle 205 or expelling fluid therefrom.

Barrel 202 includes a main tubular glass body 212 along cavity 209, an endpiece or front cap 216 that is press fit into one end of glass tube 212 and also receives needle 205, and a cap portion or back flange 203 of annular cross-section that press fits over the other end of glass body 212 and has an outer deformable lip 211.

Plunger tip 210 is an integral solid body, typically of PTFE, UHMWPE or Ekonol-filled PTFE, with a rearward open socket 215 that is deformable to receive a spigot comprising a complementary head 261 (FIG. 11) at the end of plunger stem 260 of adaptor 250. The socket may have a peripheral rim that snaps about the head but deforms to allow disengagement under sufficient axial force.

Adaptor 250 (FIG. 11) includes a central two-part elongate plunger stem 260 with an integral spigot 261 at its lower end for detachably engaging plunger tip 210 as aforedescribed. At its other end, stem 260 has an end piece 232 similar in dimensions and form to end-piece 132 of syringe component 100: it too is detachably engageable with plunger connector 60 so that plunger connector 60 and plunger stem 260 in effect form an enlarged plunger connector for operably coupling driver 402 to plunger element 210 in barrel 202 of disposable syringe component 200.

Adaptor 250 further has respective inner and outer relatively slidable sleeve members 255,257 with an internal helical compressing spring 265 between then that biases sleeve members 255,257 apart to a condition in which a head 256 on the inner sleeve member 255 abuts an enclosing back flange 258 on the outer sleeve member 257.

In this condition, an internal undercut peripheral groove 268 in outer sleeve member 257 adjacent its lower end is immediately below the lower end of inner sleeve member 255 and so can snap engage the deformable lip 211 of syringe barrel back flange 203. At the back or top end of the adaptor, a tubular shaft extension 266 of inner sleeve member 255 has, at its outer end, an end-fitting 220 of identical external profile to end-fitting 120, for similarly engaging coupling mechanism 20 and stand 600.

Syringe component 200 can be disengaged from adaptor 250 by abutting the lower end face of outer sleeve member 257 onto a stop extending about the syringe component, such as plate 620 of stand 600 (FIG. 1). Downward force by the pick-up head 300 will cause inner sleave member 255 to push against back flange 203 and disengage it from undercut groove 268: it will fall away, typically into an underlying receptacle for disposal.

Figure 2:
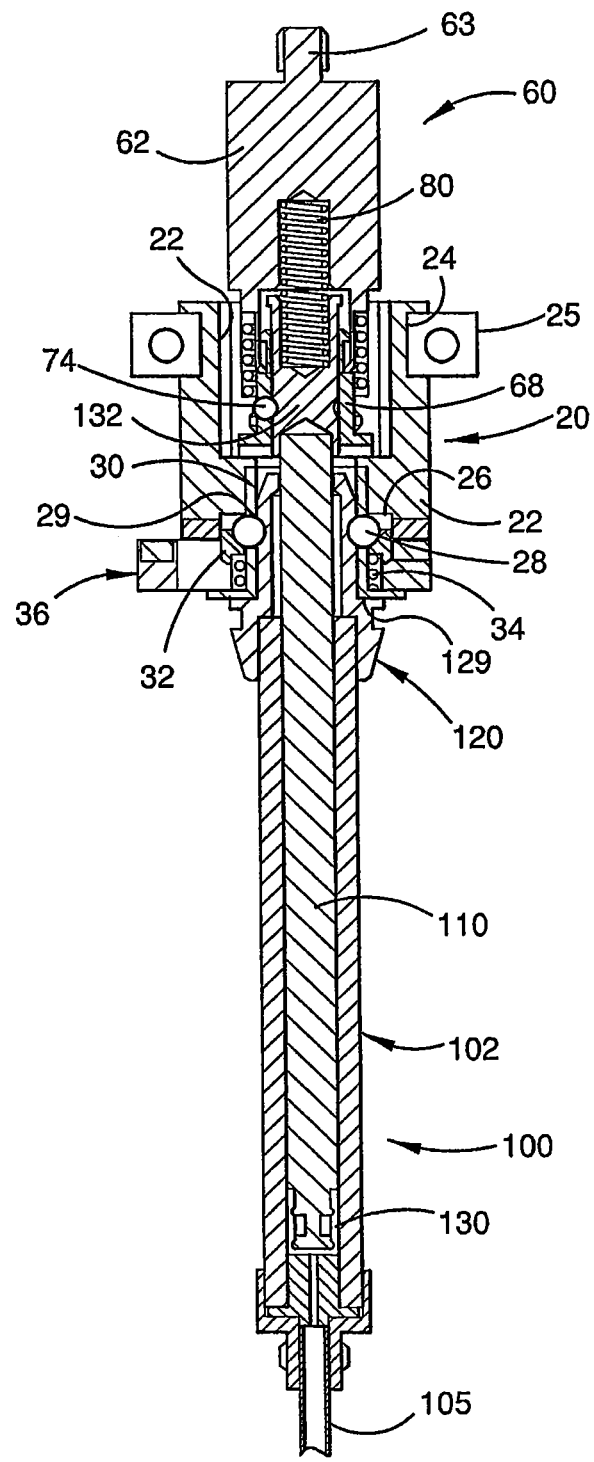
FIG. 2 is an axial cross-section of a syringe mounting apparatus according to a first embodiment of the invention with an interchangeable syringe component fully engaged in the apparatus.
Figure 13:
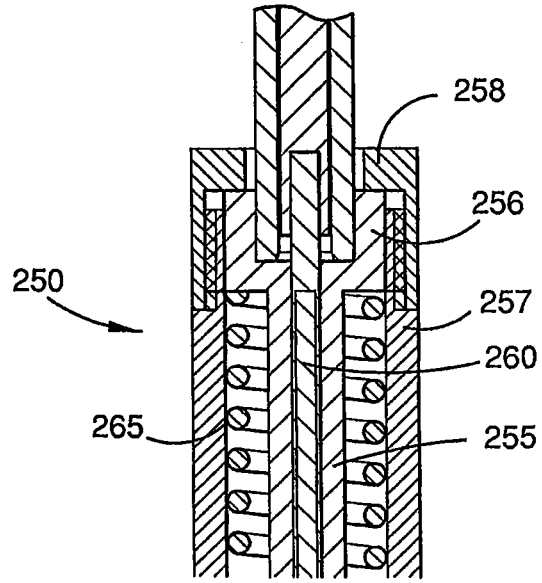
FIG. 13 is a fragmentary view of an alternative end-fitting for the adaptor depicted in FIG. 12.

Instead of the specific configuration of end fitting 220 and end-piece 232 for engaging the syringe apparatus of FIGS. 2 and 3, the adaptor 250 may have an alternative end configuration 220' such as shown in FIG. 13 for being mounted on other auto-sampler systems.

Figure 14:
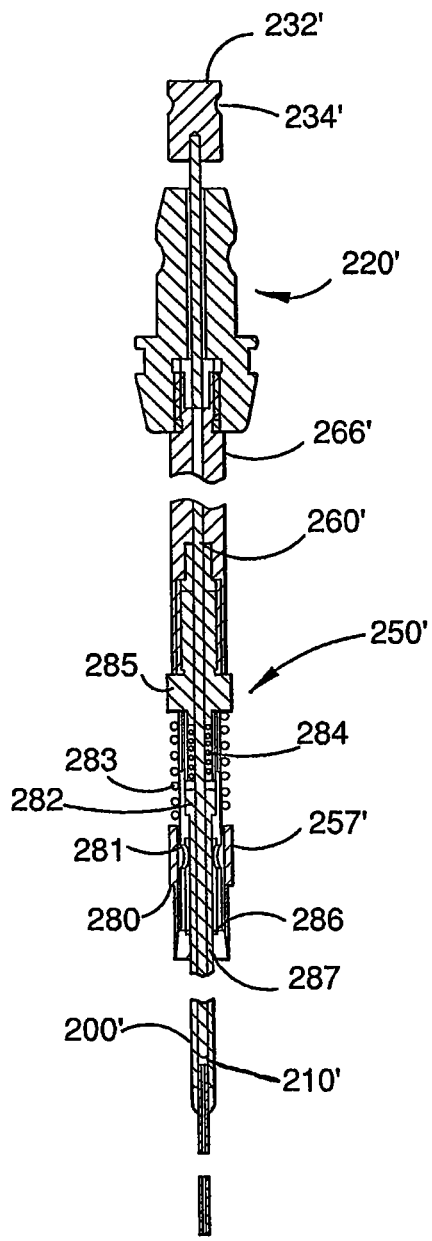
FIG. 14 is a similar view to FIG. 11, showing an alternative form of the adaptor.

FIG. 14 depicts an alternative adaptor 250' in which like parts relative to the adaptor of FIG. 11 are indicated by like primed reference numerals. In order in attach disposable syringe 200' to adaptor 250', the syringe is pushed against syringe ejection mechanism 282 which compresses spring 284. Once ejection mechanism reaches shoulder 286, outer sleeve 257' is forced downwards over slotted clutch mechanism 281. Clutch fingers of mechanism 281 tightly hold the syringe barrel in place. Plunger stem 260' is forced downwards into plunger tip 210'. The syringe can now be used as previously described. In order to decouple the syringe 200' the coupling mechanism needs to be moved to the disposal station 620. At this position the plunger drive moves upwards moving the plunger tip 210' upwards to strike face 287 of ejection mechanism 282. At this point the plunger stem 260' continues to be withdrawn and in doing so the plunger tip 210' is removed from the plunger stem 260'. Once the plunger tip 210' has been decoupled the adaptor mechanism 250' is moved downwards until face 280 of outer sleeve 257' strikes the upper face of bracket 600. Adaptor mechanism 250' continues to be forced downwards against the force of the spring 283. This action removes the force against the clutch fingers of mechanism 281 and the syringe 200' is actively pushed away from coupling mechanism 250' by ejection mechanism 282 which has spring force acting upon it from compression spring 284. The ejection mechanism 282 passes shoulder 286 and blocks the clutch fingers of mechanism 281 from closing, thus allowing a new disposable syringe 200' to be inserted.

Figure 15:
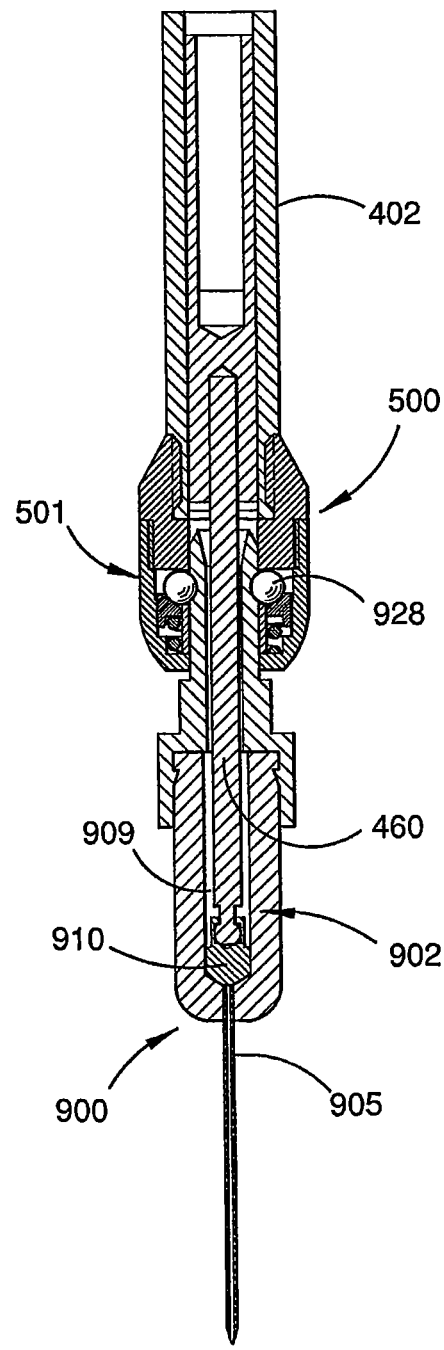
FIG. 15 is an axial cross-section of syringe mounting apparatus according to a second embodiment of the invention, suitable for direct engagement with a disposable syringe component according to an embodiment of the second aspect of the invention.

FIG. 15 depicts a second embodiment of the invention in which a coupler mechanism 500 directly engages with a disposable syringe component 900. In this embodiment, syringe component 900 is similar in principle to disposable syringe component 200, but differs in detail. Like parts are indicated by like reference numerals commencing with a "9" in place of "2".

Figure 16:
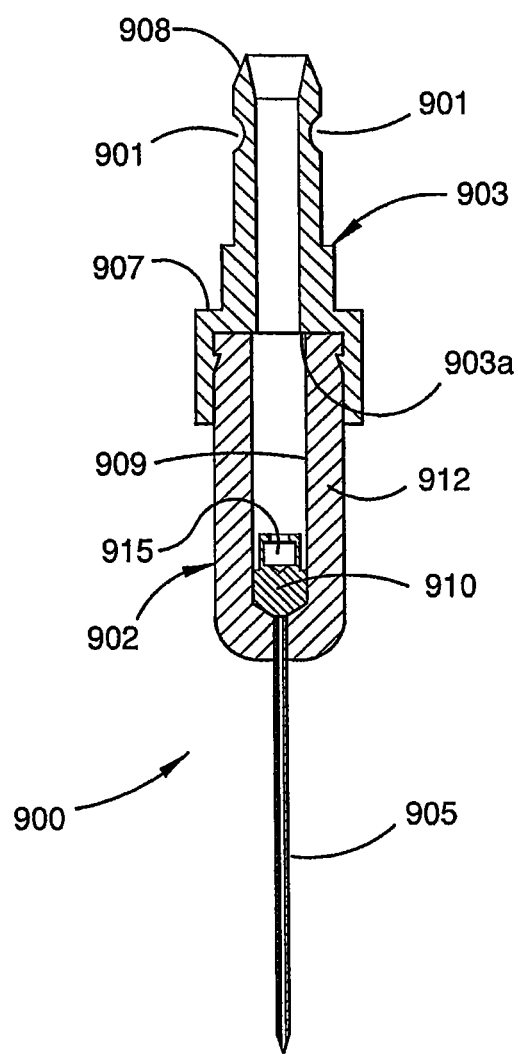
FIGS. 16 and 17 are respective axial cross-sections of the disposable syringe component and the coupling mechanism depicted in FIG. 15.

Syringe component 900 (FIG. 16) comprises a barrel 902 about an interior cavity 909, a hollow needle 905 that projects from a closed end of barrel 902 so that fluid may be drawn into cavity 909 or expelled from the cavity through the needle, and a plunger tip 910. Tip 910 is sealingly slidable in cavity 909 for drawing fluid into needle 905 or expelling fluid therefrom.

Barrel 902 includes a main tubular body 912 along cavity 903, and a cap portion 903 of annular cross-section that snap fits over the body 912 so as to define an internal annular shoulder 903a at the boundary between the two parts. The exterior of cap portion 903 has an annular shoulder 907 facing away from the needle, and a groove 901 near an externally chamfered distal end 908.

Figure 18:
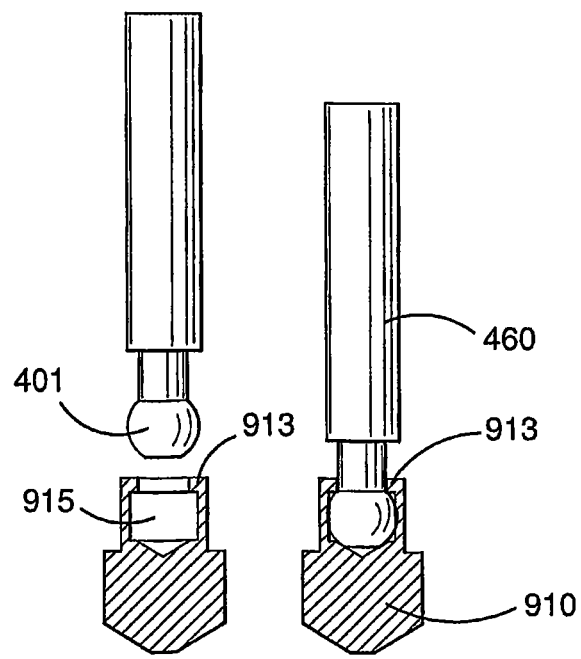
FIG. 18 comprises schematic partly sectioned views of the syringe plunger connector about to engage, and engaged with, the plunger tip within the disposable syringe component in the embodiment of FIGS. 15 to 17.

Plunger tip 910 is an integral solid body, typically of PTFE, UHMWPE or Ekonol-filled PTFE, with a rearward open socket 915 that is deformable to receive a spigot comprising a complementary head 401 at the end of a plunger connector 460, in the form of a bi-truncated sphere. The socket 915 has a peripheral rim 913 that snaps about the head (FIG. 18, right view) but deforms to allow disengagement under sufficient axial force.

Figure 17:
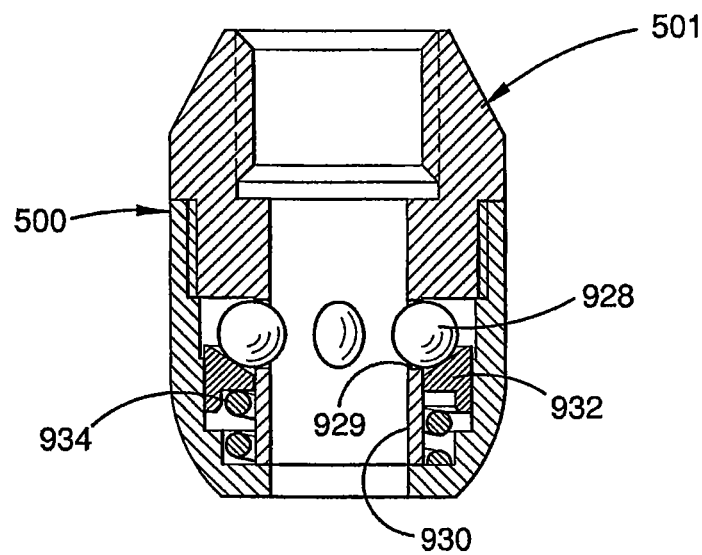

For the purposes of this embodiment, array 205 in FIG. 1 comprises disposable syringe components 900. Array 205 is positioned on the multi-axis auto-sampler 100 to facilitate aspiration of samples from vials 700 using a controller 800 of the sampler that is programmed to robotically execute a series of actions. The pick-up head 300 is moved by the controller 800 to the array of disposable elements 900 and lowered in the Z-axis so that the plunger connector 460 inserts into and engages plunger tip 910 within the disposable component 900. Simultaneously, as the plunger connector 460 inserts into the plunger 910, a two-part interlock sleeve 501 of system 500 (FIG. 17) has received cap portion 903 of the barrel 902 of disposable component 200, and multiple spring-loaded balls 928 in holes 929 on the sleeve 930 of the syringe barrel interlock engage the complementary groove 901 of the disposable component (see FIG. 15). Balls 928 are held in position by an axially moveable ring 932 that obliquely seats balls 928 and is itself engaged by a helical spring 934 to bias the balls inwardly. Balls 928 are pushed back by chamfer 908 and then drop into groove 901 to complete the connection of the two elements.

The assembly is illustrated in FIG. 15. It will be seen that the forward end of interlock sleeve 501 seats against a shoulder 907 of barrel cap portion 903, and that the distal end of cap portion 903 is a firm sliding fit within sleeve 930.

The mounted syringe component is now moved by the controller 800 to the array of sample vials 700. The syringe component 900 is lowered in the Z-axis so that the needle 905 pierces the selected vial septum 710 and travels a sufficient distance to be below the meniscus of the sample contained within the vial. A separate W-axis control 150 of the auto-sampler operates driver 402 to retract the plunger connector 460 and thereby plunger tip 910 to draw sample into the connected disposable component 900 at a predetermined rate and volume. In this case, the volume of sample drawn only contacts the features of the disposable component—the hollow needle 905, the barrel 902 and the plunger tip 910. The sample is now dispensed into a number of preferred elements such as a separate sample vial, a mixing vial or an analytical instrument.

Once the sample has been dispensed the pick-up head 300 is moved over to waste station/stand 600. Removal of the disposable syringe component 200 follows two steps:

The disposable component 200 is positioned under the fixed position 610 by placing strike surface 907 on barrel cap 903 against and below the tongue 610 of stand 600. The controller moves the pick-up head in the positive Z-axis and, on engagement of strike surface 907 with tongue 610 acting as a complementary stop, forces the features 200 and 500 to decouple.

Despite the decoupling of features 200 and 500 the disposable component is still connected to the plunger connector 460 at the plunger tip 910. Continued travel of the pick-up head 300 in the positive Z-axis now retracts the plunger tip 910 into engagement with a stop defined by annular shoulder 903a. Any further travel of the plunger driver 402 will result in the decoupling, resulting in the disposable component falling freely into a waste bin below waste system 600. The plunger tip 910 remains within the element 200 on disposal.

The process can now be repeated using a new disposable syringe component 200 for each sample 700.

In a modification (not illustrated), any of the illustrated syringes may be adapted for solid phase microextraction (SPME) analysis by incorporating a solid phase material within barrel 102,202,902 (e.g. as a porous plug, coating or filter) or within a needle (e.g. as an insert, coated cylinder or interchangeable cartridge). The solid phase material may be, e.g., a silica-based material, a molecular imprinting polymer, polydimethylsiloxane or polystyrene-divinylbenzene.

The invention claimed is:

1. A syringe handling system comprising:
a multi-axis auto-sampler including a syringe pick-up head on the auto-sampler moveable laterally and vertically in a work space;
a plunger driver;
a control of the auto-sampler that operates the plunger driver; and
a syringe mounting apparatus on the syringe pick-up head that includes a coupling arrangement and a plunger connector carried by the plunger driver;
wherein the coupling arrangement has a housing to receive a barrel of a syringe component, the housing mounted for being moved down onto and about the end of the barrel, and the coupling arrangement further having a mechanism configured to detachably engage the barrel and thereby interchangeably retain the syringe component as the housing is so moved;
and wherein the plunger connector is receivable in a concentric cavity in said housing for operably detachably coupling the plunger driver to a plunger element carried in the barrel of the syringe component when the syringe component is interchangeably retained by said mechanism, which plunger connector is moveable onto the end of said plunger element until said plunger connector detachably engages the plunger element in a manner allowing said plunger driver to thereafter effect reciprocatory movement of the plunger element longitudinally of said barrel for drawing fluid into or expelling fluid from the syringe component.

2. A syringe handling system according to claim 1, wherein said control of the auto-sampler is programmable or programmed for selectively effecting said movement of the pick-up head laterally and vertically in said work space, for operating said plunger driver, and to selectively engage and disengage successive syringe components.

3. A syringe handling system according to claim 1 including a plurality of disposable syringe components detachably engageable by and thereby interchangeably retainable by said mechanism of the coupling arrangement, which disposable syringe components each comprise:
a syringe barrel;
a hollow needle projecting from an end of the barrel;
a syringe plunger tip sealingly slidable in the barrel for drawing fluid into the needle or expelling fluid through the needle; and
a formation on the plunger tip detachably engageable with the plunger connector for driving the plunger tip to slide in the barrel.

4. A syringe handling system according to claim 1 in combination with an analyser.

5. A syringe handling system according to claim 4 wherein the analyser is one or more of a gas chromatograph, a liquid chromatograph, a mass spectrometer and any combination of two or more of these.

6. A handling system according to claim 1 for use with syringe components having a said plunger element in the form of a plunger tip, wherein said plunger connector further includes an elongate plunger arranged to reciprocate longitudinally through the coupling arrangement and within the barrel of the syringe component, which plunger has a head portion that detachably engages the plunger tip within the barrel.

7. A handling system according to claim 6, for use with a syringe component having a said plunger element that projects from said barrel, wherein said plunger connector comprises a housing to receive said plunger element and is configured to detachably engage the plunger element.

8. A syringe handling system according to claim 6 wherein said control of the auto-sampler is programmable or programmed for selectively effecting said movement of the pick-up head laterally and vertically in said work space, for operating said plunger driver, and to selectively engage and disengage successive syringe components.

9. A syringe handling system according to claim 1 including a plurality of re-usable syringe components detachably engageable by and thereby interchangeably retainable by said mechanism of the coupling arrangement.

10. A syringe handling system according to claim 9 including a plurality of disposable syringe components each in combination and one or more adaptors each having a first portion interchangeably receivable by and detachably engageable with said coupling arrangement, and a second portion detachably engageable with of any one of said disposable syringe components, said adaptor having a longitudinally extending cavity therethrough for said plunger element and/or plunger connector.

11. A syringe handling system according to claim 10 wherein said first portion of the adaptor is interchangeable for other syringe mounting formations.

12. A syringe handling system according to claim 10 wherein said adaptor comprises respective inner and outer relatively slidable sleeve members arranged whereby movement of one of the sleeve members when the other is against a stop is effective to disengage a barrel of a retained syringe component from a formation in said other sleeve member.

13. A handling system according to claim 1 wherein said mechanism includes a sleeve and first resiliently retractable elements or formations retained by the sleeve engageable with co-operating formations on a barrel of a syringe component.

14. A handling system according to claim 13 wherein said first resiliently retractable elements comprise plural spaced spring biased balls.

15. A handling system according to claim 13 further including a slide member to lock said first resiliently retractable elements or formations against retraction, whereby to lock a barrel engaged thereby in said mechanism.

16. A handling system according to claim 13 for use with syringe components having a said plunger element in the form of a plunger tip, wherein said plunger connector further includes an elongate plunger arranged to reciprocate longitudinally through the coupling arrangement and within the barrel of the syringe component, which plunger has a head portion that detachably engages the plunger tip.

17. A handling system according to claim 13, for use with a syringe component having a said plunger element that projects from said barrel, wherein said plunger connector comprises a housing to receive said plunger element and is configured to detachably engage the plunger element.

18. A syringe handling system according to claim 13 wherein said control of the auto-sampler is programmable or programmed for selectively effecting said movement of the pick-up head laterally and vertically in said work space, for operating said plunger driver, and to selectively engage and disengage successive syringe components.

19. A handling system according to claim 1, for use with a syringe component having a said plunger element that projects from said barrel, wherein said plunger connector comprises a housing to receive said plunger element and is configured to detachably engage the plunger element.

20. A handling system according to claim 5 wherein said housing is configured to detachably engage the plunger element by comprising a sleeve assembly and second resiliently retractable elements or formations within the sleeve assembly engageable with co-operating formations on the plunger element.

21. A handling system according to claim 20 wherein said second resiliently retractable elements comprise plural spaced spring biased balls.

22. A handling system according to claim 19 including an adaptor having a first portion interchangeably receivable by and detachably engageable with said coupling arrangement, and a second portion detachably engageable with a barrel of a syringe component too small to be interchangeably retained by said mechanism, said adaptor having a longitudinally extending cavity therethrough for said plunger element and/or plunger connector.

23. A handling system according to claim 22 wherein said adaptor comprises respective inner and outer relatively slidable sleeve members arranged whereby movement of one of the sleeve members when the other is against a stop is effective to disengage a barrel of a retained syringe component from a formation in said other sleeve member.

24. A handling system according to claim 22 for use with syringe components having a said plunger element in the form of a plunger tip, wherein said plunger connector further includes an elongate plunger mounted in said adaptor cavity and arranged to reciprocate longitudinally through the coupling arrangement and within the barrel of the syringe component, which plunger has a head portion that detachably engages the plunger tip within the barrel.

25. A handling system according to claim 22, wherein said first portion of the adaptor is interchangeable for other syringe mounting formations.

* * * * *